United States Patent
Murakami et al.

(10) Patent No.: US 10,774,199 B2
(45) Date of Patent: Sep. 15, 2020

(54) ADDITIVE FOR RUBBER

(71) Applicant: SUMITOMO SEIKA CHEMICALS CO., LTD., Kako-gun, Hyogo (JP)

(72) Inventors: Shinya Murakami, Kako-gun (JP); Hideaki Nishiguchi, Osaka (JP); Takehiro Hiyama, Kako-gun (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 177 days.

(21) Appl. No.: 15/781,822

(22) PCT Filed: Dec. 7, 2016

(86) PCT No.: PCT/JP2016/086425
§ 371 (c)(1),
(2) Date: Jun. 6, 2018

(87) PCT Pub. No.: WO2017/099138
PCT Pub. Date: Jun. 15, 2017

(65) Prior Publication Data
US 2018/0362732 A1 Dec. 20, 2018

(30) Foreign Application Priority Data
Dec. 8, 2015 (JP) .................... 2015-239098
Mar. 31, 2016 (JP) .................... 2016-073331

(51) Int. Cl.
| C08K 5/372 | (2006.01) |
| C07C 323/12 | (2006.01) |
| C08L 7/00 | (2006.01) |
| C08G 75/14 | (2006.01) |
| C08L 81/04 | (2006.01) |
| C08L 21/00 | (2006.01) |
| C08L 9/06 | (2006.01) |

(52) U.S. Cl.
CPC ............ C08K 5/372 (2013.01); C07C 323/12 (2013.01); C08G 75/14 (2013.01); C08L 7/00 (2013.01); C08L 9/06 (2013.01); C08L 21/00 (2013.01); C08L 81/04 (2013.01); C08L 2201/08 (2013.01)

(58) Field of Classification Search
CPC ............... C08K 5/372; C07C 323/12
See application file for complete search history.

(56) References Cited

U.S. PATENT DOCUMENTS

| 3,523,985 A | 8/1970 | Marrs |
| 3,706,610 A | 12/1972 | Ferguson |
| 3,869,435 A | 3/1975 | Trivette, Jr. |
| 3,979,369 A | 9/1976 | Trivette, Jr. |
| 4,085,094 A | 4/1978 | Lawrence |
| 4,421,899 A | 12/1983 | Yamazaki et al. |
| 6,079,468 A | 6/2000 | D'Sidocky et al. |
| 2006/0094831 A1 | 5/2006 | Choi et al. |
| 2011/0301280 A1 | 12/2011 | Kushida |

FOREIGN PATENT DOCUMENTS

| CN | 101423628 A | 5/2009 |
| JP | 48-62844 A | 9/1973 |
| JP | S57-170939 A | 10/1982 |
| JP | 58-167634 A | 10/1983 |
| JP | 59-213745 A | 12/1984 |
| JP | 62-100542 A | 5/1987 |
| JP | 10-77361 A | 3/1998 |
| JP | 11-293036 A | 10/1999 |
| JP | 2002-155093 A | 5/2002 |
| JP | 2010174237 A * | 8/2010 |
| JP | 2011-252124 A | 12/2011 |
| JP | 2014-210870 A | 11/2014 |
| RU | 2 099 361 C1 | 12/1997 |
| WO | 2018/074570 A1 | 4/2018 |

OTHER PUBLICATIONS

Machine translation of JP 2010-174237, published Aug. 12, 2010. (Year: 2010).*
International Search Report dated Feb. 14, 2017, issued in counterpart International Application No. PCT/JP2016/086425 (2 pages).
Office Action dated Dec. 18, 2019, issued in counterpart CN Application No. 201680071659.3, with English translation. (12 pages).
Notification of Transmittal of Translation of the International Preliminary Report on Patentability (Form PCT/IB1338) issued in counterpart International application No. PCT/JP2016/086425 dated Jun. 21, 2018, with Forms PCT/IB/373 and PCT/ISA/237 (8 pages).
Extended (Supplementary) European Search Report dated Jul. 22, 2019, issued in counterpart EP application No. 16873031.5. (8 pages).
Office Action dated Mar. 3, 2020, issued in counterpart to TW Application No. 105140413. (9 pages).

(Continued)

*Primary Examiner* — Vickey Nerangis
(74) *Attorney, Agent, or Firm* — Westerman, Hattori, Daniels & Adrian, LLP

(57) ABSTRACT

Provided is an additive for rubber that contains a sulfide composition, wherein the sulfide composition in the additive for rubber contains a sulfide compound having the repeating units shown by formula (1), the amount of repeating units (1) in which X=2 is at least 45 molar parts per 100 molar parts of repeating units (1) in the sulfide compound, and the number n of repeating units (1) in the sulfide compound is from 1 to 400, whereby an additive for rubber capable of imparting excellent heat resistance is provided. Also provided is a rubber composition that contains said additive for rubber.

[Chemical formula 1]

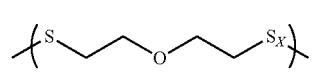

wherein X is 1, 2 or 3.

20 Claims, 1 Drawing Sheet

(56) References Cited

OTHER PUBLICATIONS

Office Action dated Mar. 31, 2020, issued in counterpart JP application No. 2017-555108, with English translation. (8 pages).

\* cited by examiner

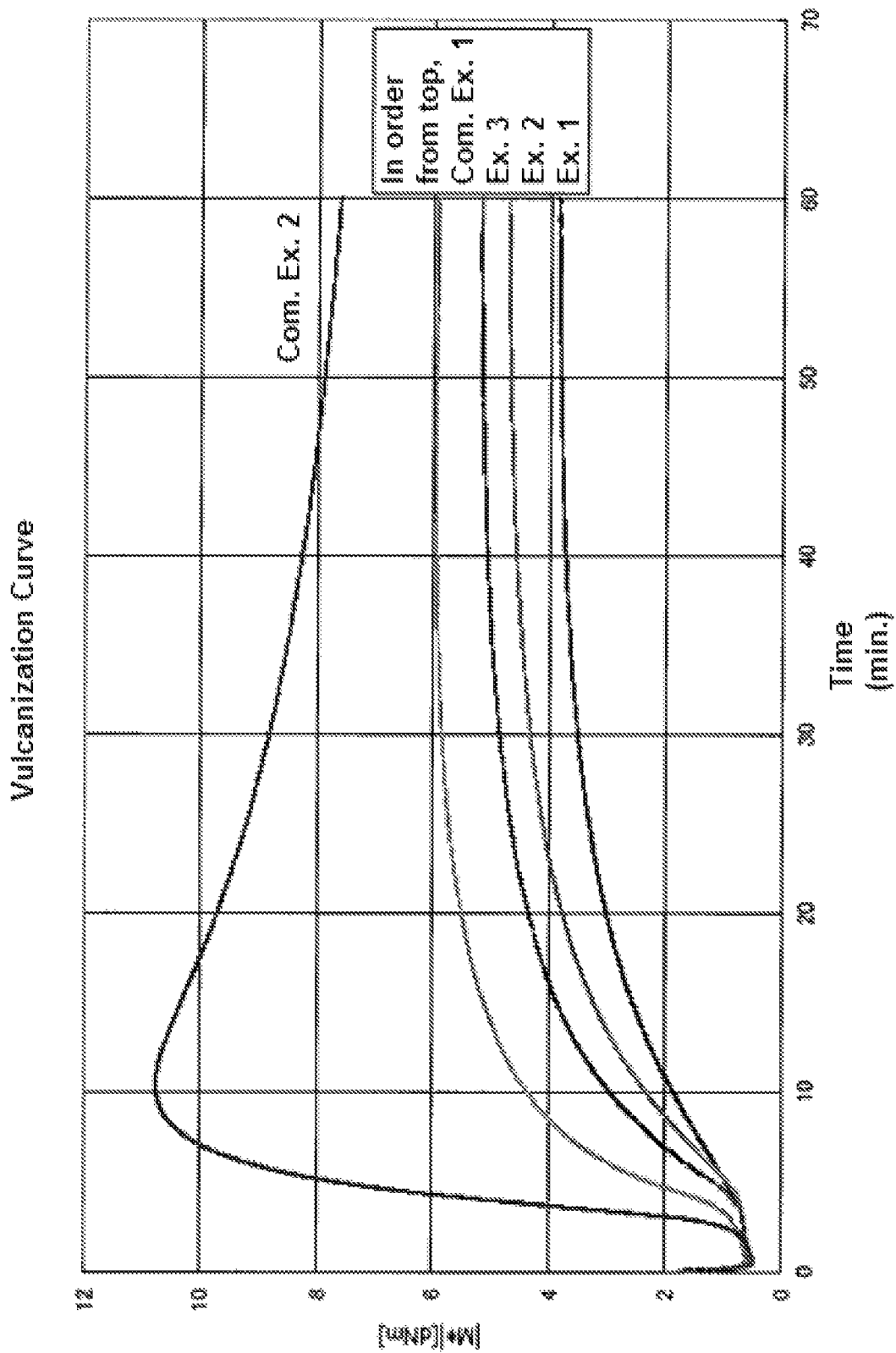

ADDITIVE FOR RUBBER

TECHNICAL FIELD

The present invention relates to an additive for rubber and a rubber composition comprising the additive for rubber.

BACKGROUND ART

For improving performance of rubber products, for example, use of sulfur as a vulcanizing agent is known. In recent years, an additive comprising benzothiazole in the chemical structure (for example, Patent Document 1) or an additive comprising a cyclic polysulfide (for example, Patent Document 2) has been disclosed for improving the physical properties of the rubber product.

RELATED ART DOCUMENT

Patent Literature

Patent Document 1: JP H11-293036A
Patent Document 2: JP 2014-210870A

SUMMARY OF THE INVENTION

Disclosure of the Invention

However, the additives comprising benzothiazole in the chemical structure may cause long-term influences, for example, on organisms and plants due to the chemical structure. Accordingly, it is desired to reduce the amount of the additives comprising benzothiazole in the chemical structure.

In addition, rubber products are required to have both good heat resistance and mechanical properties depending on the use.

Further, the additives comprising the cyclic polysulfide may cause an odor problem due to the relatively small molecular weight. Furthermore, in the step of producing the additive comprising the cyclic polysulfide disclosed in such as Patent Document 2, a large amount of salt is produced as a by-product, thereby the salt may also be mixed in the produced additive and the mechanical properties of rubber may be deteriorated.

An object of the present invention is to provide an additive for rubber capable of imparting good heat resistance.

Means to Solve the Problems

The present invention relates to the followings.
[1] An additive for rubber comprising a sulfide composition,
wherein the sulfide composition comprises a sulfide compound having a repeating unit represented by formula (1),
wherein, in the sulfide compound, the amount of repeating unit (1) having X=2 is at least 45 parts by mol per 100 parts by mol of the total amount of repeating unit (1),
wherein n meaning the number of repeating unit (1) in the sulfide compound is 1 to 400:

[Chemical formula 1]

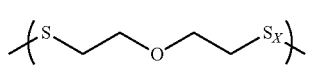
(1)

wherein X is 1, 2 or 3.

[2] The additive for rubber according to [1],
wherein, in the sulfide compound, the amount of repeating unit (1) having X=2 is at least 50 parts by mol per 100 parts by mol of the total amount of repeating unit (1).
[3] The additive for rubber according to [1] or [2],
wherein, in the sulfide compound, the amount of repeating unit (1) having X=1 is 1 parts by mol to 40 parts by mol per 100 parts by mol of the total amount of repeating unit (1).
[4] The additive for rubber according to any one of [1] to [3],
wherein the sulfide compound further has a repeating unit represented by formula (2),
wherein the amount of repeating unit (2) is at most 10 parts by mol per 100 parts by mol of the total amount of repeating unit (1) comprised in the sulfide compound:

[Chemical formula 2]

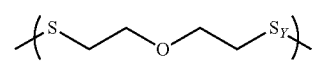
(2)

wherein Y is 0 or an integer of at least 4.
[5] A rubber composition comprising the additive for rubber according to anyone of [1] to [4] and natural rubber and/or synthetic rubber.

Effect of the Invention

According to the present invention, an additive for rubber capable of imparting good heat resistance and a rubber composition comprising the additive for rubber can be obtained.

BRIEF DESCRIPTION OF THE DRAWINGS

FIG. 1 Vulcanization curve according to a rubber composition comprising natural rubber (NR) is shown.

MODE FOR CARRYING OUT THE INVENTION

Hereinafter, the sulfide compound having the repeating unit represented by formula (1) will be described. Incidentally, the description concerning formula (1) can be referred to for formula (2). Similarly, the description concerning formula (2) may be referred to for formula (1) and the present invention is not to be construed as limited thereto.

The additive for rubber of the present invention relates to additive for rubber comprising a sulfide composition,
wherein the sulfide composition comprises a sulfide compound having a repeating unit represented by formula (1),
wherein, in the sulfide compound, the amount of repeating unit (1) having X=2 is at least 45 parts by mol per 100 parts by mol of the total amount of repeating unit (1)
wherein n meaning the number of repeating unit (1) in the sulfide compound is 1 to 400:

[Chemical formula 3]

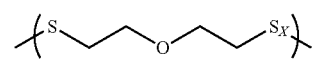
(1)

wherein X is 1, 2 or 3. In the present invention, X is an integer.

As described above, the additive for rubber of the present invention comprises a sulfide composition, and the sulfide composition comprises a compound having a repeating unit represented by formula (1). Here, the compound having a repeating unit represented by formula (1) according to the present invention is a sulfide compound having a specific repeating unit represented by the above formula (1). In the present specification, the "parts by mol" relating to "the amount of repeating unit" means the number (ratio) of unit of X=1, 2 or 3 present in the sulfide compound having the repeating unit (1).

The sulfide composition according to the present invention may comprise an arbitrary sulfide compound in addition to the sulfide compound having the repeating unit (1). The arbitrary sulfide compound is not particularly limited as far as it is a sulfide compound other than the sulfide compound having the repeating unit (1). For example, other chain or cyclic sulfide compounds may be used. However, an arbitrary sulfide compound can be included within the range not to impair the effects of the present invention. For example, the sulfide composition according to the present invention may comprise a sulfide compound having a repeating unit having X=4, 5 or the like in formula (1) in addition to the sulfide compound having the repeating unit (1).

The lower limit of the number n of the repeating unit (1) comprised in the sulfide compound having the repeating unit (1) is preferably 2, more preferably 6, and still more preferably 10. The preferable upper limit of the number n of the repeating unit (1) comprised in the sulfide compound having the repeating unit (1) is 350, more preferably 300, and even more preferably 200.

The sulfide compound having the repeating unit (1) may further comprise a repeating unit represented by formula (2):

[Chemical formula 4]

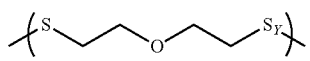

(2)

wherein Y is 0 or an integer of at least 4.

In the sulfide compound, the amount of repeating unit (2) may be, for example, at most 15 parts by mol, preferably at most 10 parts by mol, and more preferably at most 7 parts by mol and additionally may be preferably at least 0 parts by mol, more preferably at least 3 parts by mol, per 100 parts by mol of the total amount of repeating unit (1).

Y is an integer, for example, 0 or an integer from 4 to 8, preferably 0 or an integer from 4 to 7.

When the number of repeating unit (2) comprised in the sulfide compound having the repeating unit (1) is m, the lower limit of n+m which is the total of the number of repeating unit (1) and the repeating unit (2) comprised in the sulfide compound having the repeating unit (1) is preferably 2, more preferably 6, and further preferably 10. The upper limit of n+m which is the total of the number of repeating unit (1) and the repeating unit (2) comprised in the sulfide compound having the repeating unit (1) is preferably 350, more preferably 300 and further preferably 200.

In the sulfide compound having the repeating unit (1), the parts of the repeating unit (1) and the repeating unit (2) may be at least 75 mass %, for example, at least 85 mass %, particularly at least 95 mass %. The sulfide compound having the repeating unit (1) may only consist of the repeating unit (1) and the repeating unit (2).

When the total amount of a sulfide compound comprised in the sulfide composition according to the present invention is 100 mol, the sulfide compound having the repeating unit (1) is comprised in total, for example, in the range of 80 to 100 mol, and may be comprised in the range of 80 to 95 mol, in the sulfide composition.

When the total amount of the sulfide compound comprised in the sulfide composition according to the present invention is 100 mass %, the amount of sulfide compound having the repeating unit (1) is comprised in total, for example, at least 5 mass %, at least 25 mass %, at least 50 mass %, at least 75 mass %, at least 90 mass % in the sulfide composition.

When the total amount of the additive for rubber of the present invention is 100 mass %, the content of the sulfide composition according to the present invention is preferably at least 0.001 mass %, more preferably at least 0.1 mass %, further preferably is 0.1 to 50 mass %, and more preferably 1 to 30 mass %.

For example, the content of the sulfide compound having the repeating unit represented by the above formula (1) and/or formula (2) in the additive for rubber is preferably at least 0.1 mass %, more preferably 0.1 to 99 mass %, further preferably 1 to 99 mass % per the total amount of additive for rubber of the present invention. In a preferred embodiment, the content of the sulfide compound having the repeating unit represented by the above formula (1) and/or (2) in the additive for rubber is 1 to 30 mass %.

When the content of the sulfide compound having the repeating unit represented by formula (1) and/or formula (2) is within the above range, the effect of blending the additive for rubber of the present invention is sufficiently exhibited thereby improvement of the effect corresponding to the amount can be shown, which is economically advantageous.

By comprising the sulfide compound having the repeating unit represented by formula (1) and/or formula (2) within such a range, the additive for rubber of the present invention can impart superior mechanical properties such as tensile stress, elongation at break and compression set; superior physical properties such as heat resistance, reduction in hysteresis loss, cold resistance, aging resistance and ozone resistance; superior electrical properties, oil resistance and chemical resistance.

In the present invention, per 100 parts by mol of the total amount of repeating unit (1) comprised in the sulfide compound having the repeating unit (1), the repeating unit having X=2 in the sulfide compound having the repeating unit (1) is at least 45 parts by mol.

When the amount of repeating unit (1) having X=2 is at least 45 parts by mol, an additive for rubber capable of imparting good aging resistance and heat resistance can be obtained. Also, since the amount of repeating unit (1) having X=2 is within such a range, the additive for rubber of the present invention can impart superior mechanical properties such as tensile stress, elongation at break and compression set; superior physical properties such as heat resistance, reduction in hysteresis loss, cold resistance, aging resistance and ozone resistance; superior electrical properties, oil resistance and chemical resistance.

In a preferred embodiment, per 100 parts by mol of the total amount repeating unit (1), the amount of repeating unit (1) having X=2 comprised in the sulfide compound having the repeating unit (1) is preferably at least 50 parts by mol, more preferably at least 55 parts by mol, further preferably at least 60 parts by mol. The upper limit of the amount of repeating unit (1) having X=2 is not particularly limited, but it is preferably at most 100 parts by mol, more preferably at most 99 parts by mol, further preferably at most 95 parts by mol, for example, at most 80 parts by mol.

In a preferred embodiment, per 100 parts by mol of the total amount of repeating unit (1) comprised in the sulfide compound having the repeating unit (1), the amount of repeating unit (1) having X=1 in the sulfide compound having the repeating unit (1) is preferably 0.1 parts by mol to 40 parts by mol, more preferably 1 parts by mol to 40 parts by mol, further preferably 1 parts by mol to 20 parts by mol.

In a preferred embodiment, per 100 parts by mol of the total amount of repeating unit (1) comprised in the sulfide compound having the repeating unit (1), the amount of repeating unit (1) having X=3 in the sulfide compound having the repeating unit (1) is preferably 0.1 parts by mol to 54 parts by mol, more preferably 4 parts by mol to 54 parts by mol, further preferably 4 parts by mol to 40 parts by mol.

In a preferred embodiment, per 100 parts by mol of the total amount of repeating unit (1) comprised in the sulfide compound having the repeating unit (1), the amount of the repeating unit (1) having X=1 parts by mol is preferably 1 to 40 parts by mol and the amount of repeating unit (1) having X=2 is preferably 45 parts by mol to 95 parts by mol in the sulfide compound having the repeating unit (1).

More preferably, per 100 parts by mol of the total amount of repeating unit (1) comprised in the sulfide compound having the repeating unit (1), the amount of repeating unit (1) comprised in the sulfide compound having the repeating unit (1) having X=1 is 1 parts by mol to 20 parts by mol and the amount of repeating unit (1) having X=2 is 55 parts by mol to 95 parts by mol.

In a preferred embodiment, the amount of repeating unit (1) having X=3 in the sulfide compound having the repeating unit (1) is preferably larger than the amount of repeating unit (1) having X=1, more preferably, the ratio the amount of repeating unit having X=3: the amount the repeating unit (1) having X=1 is in the range of 1.1:1 to 10:1. By comprising the repeating unit (1) having X=1 and X=3 in the range as described above in the sulfide compound having the repeating unit (1), an additive for rubber capable of imparting better aging resistance and heat resistance can be obtained.

In any of the embodiments, per 100 parts by mol of the total amount of repeating unit (1) comprised in the sulfide compound having the repeating unit (1), the amount of repeating unit (1) having X=1 and repeating unit (1) having X=3 is determined so that the amount of repeating unit (1) having X=2 in the sulfide compound having the repeating unit (1) is at least 45 parts by mol, preferably at least 50 parts by mol, more preferably at least 55 parts by mol, further preferably at least 60 parts by mol.

Since the amount of repeating unit (1) is in such a range, for example, an additive for rubber capable of imparting better heat resistance and further imparting aging resistance can be obtained. In addition, additives for rubber having improved anti-reversion property and improved mechanical property can be obtained.

By having the repeating unit having X=1 (disulfide) within the above range, good heat resistance can be provided. Further, since the compound having the repeating unit (1) having X=1 is a more stable compound, it is predicted that it may not badly affect, for example, on the rubber composition.

The method for producing the sulfide compound having the repeating unit represented by formula (1) and/or formula (2) according to the present invention is not particularly limited. For example, it can be produced by reacting sulfur monochloride with chlorine gas to prepare an intermediate product and reacting the intermediate product with bis(2-mercaptoethyl)ether as a mercapto group-comprising compound in an arbitrary solvent.

The solvent is not particularly limited. Examples thereof include hydrocarbon type organic solvents such as hexane, benzene, toluene and xylene; ether type organic solvents such as diethyl ether and tetrahydrofuran; halogenated hydrocarbon type organic solvents such as dichloromethane, chloroform and monochlorobenzene; and acetonitrile.

The additive for rubber of the present invention may comprise further known additives and/filler in addition to a sulfide composition comprising a compound having a repeating unit represented by the above formula (1) and/or formula (2). The additive may be diluted with oil, an ester compound, or an organic compound which does not inhibit the effect of the additive for rubber, if desired.

The additive for rubber of the present invention is an additive capable of improving the properties of the rubber composition and the rubber product. Preferably, the additive for rubber of the present invention can be used as a vulcanizing agent, a vulcanization accelerator, an antioxidant, a heat resistance improver, a plasticizer, a viscosity modifier, a molecular weight regulator and a stabilizer. More preferably, since the additive for rubber of the present invention can, for example, improve heat resistance and can impart good mechanical strength on the basis of its good properties, it can be used as a vulcanizing agent, a vulcanization accelerator, an antioxidant or a heat resistance improver.

The method of using the additive for rubber of the present invention is not particularly limited. For example, the additive for rubber of the present invention may be blended with natural rubber and/or synthetic rubber and used as a rubber composition.

In addition, since the additive for rubber of the present invention can impart good heat resistance, aging resistance and mechanical properties even when used alone, other additives may or may not be used in combination.

The rubber composition in the present invention comprises at least an additive for rubber comprising a sulfide composition comprising a compound having the repeating unit (1) and a rubber component which is a natural rubber and/or a synthetic rubber.

The additive for rubber comprising a sulfide composition comprising a compound having a repeating unit represented by formula (1) and/or formula (2) is comprised in an amount of preferably 0.5 to 20 mass parts, more preferably 1 to 15 mass parts, still more preferably 1 to 10 mass parts per 100 mass parts of the rubber component in the rubber composition. The amount of the additive for rubber to be added can be appropriately selected depending on the type of natural rubber and/or synthetic rubber used and required physical properties.

When the content of the additive for rubber comprising the sulfide composition comprising the compound having the repeating unit represented by formula (1) and/or formula (2) is within the above-mentioned range, better heat resistance, aging resistance and mechanical properties can be imparted to the rubber composition, the rubber product and the like.

[Rubber Component]

As the rubber component, natural rubber and/or synthetic rubber is preferable. The synthetic rubber is preferably a diene synthetic rubber. Examples of the diene synthetic rubber include polyisoprene synthetic rubber (IR), polybutadiene rubber (BR), styrene-butadiene copolymer rubber (SBR), acrylonitrile-butadiene copolymer rubber (NBR), chloroprene rubber (CR), butyl rubber (IIR) and the like. The natural rubber and these diene type synthetic rubber components may be used singly or in combination of at least two kinds.

[Further Additive/Filler]

The rubber composition of the present invention comprises an additive for rubber comprising a sulfide composition comprising a compound having a repeating unit represented by the above formula (1) and/or formula (2) and natural rubber and/or synthetic rubber, and may further comprise known additives and/or fillers.

The rubber composition of the present invention may comprise preferably 10 to 160 mass parts of further additives and/or fillers in total per 100 mass parts of the rubber component. Further additives and/or fillers may be used singly or in combination. The mixing ratio of further additives and/or filler combinations is not limited.

As the further additives, known additives in the technical field can be used and examples thereof include a vulcanizing agent, a vulcanization accelerator, an antioxidant, a heat resistance improver, a plasticizer, a viscosity modifier, a molecular weight modifier, a stabilizer, a processing aid, a vulcanization aid, a white filler, a reactive monomer and a foaming agent. For example, even when an additive for rubber comprising a sulfide composition comprising a compound having a repeating unit represented by formula (1) and/or formula (2) of the present invention is used as a vulcanizing agent, the rubber composition of the present invention may comprise other vulcanizing agent.

The filler may be, for example, a filler such as an inorganic filler or carbon black. It is preferable to use silica as the inorganic filler. The examples of silica include wet precipitation method silica and dry method silica, and wet precipitation method silica is particularly preferable.

Carbon black enhances mechanical performance and improves processability and the like, and it is preferable to use known carbon black by appropriately selecting ranges of such as $I_2$ adsorption amount, CTAB specific surface area, $N_2$ adsorption amount and DBP adsorption amount. As carbon black, known ones such as SAF, ISAF, ISAF-LS, HAF, HAF-HS, HAF-LS and the like can be appropriately selected and used. Considering the abrasion resistance, ISAF, SAF and HAF having a fine particle diameter are preferable.

As the filler, silica alone may be used, or a combination of carbon black and silica may be used. In this case, the mixing ratio of carbon black and silica [carbon black]/[silica] is preferably from 0.04 to 6.0, more preferably from 0.1 to 3.0, further preferably from 0.1 to 1.0 by mass ratio.

The rubber composition of the present invention can be prepared by blending an additive for rubber comprising a sulfide composition comprising a compound having a repeating unit represented by formula (1) and/or formula (2) and a natural rubber and/or a synthetic rubber in addition to further additives and/or fillers as needed, according to a known method. Preferably the rubber composition is prepared preferably in the range from 20 to 100° C., more preferably in the range from 20 to 80° C. By preparing a rubber composition in such a temperature range, it can be blended without progressing crosslinking by the additive for rubber of the present invention.

The rubber composition of the present invention can be used as a raw material for various rubber products. Examples of rubber products include vibration isolating rubber; vibration isolating materials such as engine mounts, stabilizer bushings and suspension bushes used for vehicles; computer hard disk control damper; vibration control dampers for home appliances such as washing machines; vibration control devices such as damping walls for buildings, vibration control dampers and applications of the seismic isolation device in building and housing fields; furthermore, general and industrial products such as vehicle parts, tires, footwear, hoses, belts, air springs and anti-skid sheets. By comprising the additive for rubber comprising the rubber composition comprising the compound having a repeating unit represented by formula (1), the rubber composition of the present invention can provide good aging resistance, heat resistance and mechanical properties. The rubber composition of the present invention is preferably applied to a vibration isolating material for an engine mount and the like for a vehicle and the like.

EXAMPLE

The present invention will be described more specifically by the following examples, but the present invention is not limited thereto. "Parts" and "%" in the examples are based on mass unless otherwise indicated.

Synthesis Example 1 Synthesis of Sulfide Compound Having Repeating Unit Represented by Formula (1)

Poly(4-oxa-1,7,8-polythiaoctamethylene) was synthesized through the process outlined in the following.

More specifically, 80 g of sulfur monochloride and 0.02 g of iron powder were placed in a 100 mL four-necked flask, and further 43 g of chlorine gas was blown into the flask. Thereafter, iron powder was removed to obtain 118 g of sulfur dichloride.

Next, 150 g of bis(2-mercaptoethyl)ether, 370 g of toluene and 112 g of synthesized sulfur dichloride were added to a 1000 mL four-necked flask. The solvent of the obtained reaction liquid was removed by distillation under reduced pressure to obtain poly(4-oxa-1,7,8-polythiaoctamethylene). The structure was confirmed by GPC and $^1$H-NMR.

As to the amount of each repeating unit in the sulfide compound obtained by the above process, per 100 parts by mol of the total amount of repeating unit (1), the amount of disulfide (repeating unit having X=1 in formula (1)) was 10 parts by mol, the amount of trisulfide (repeating unit having X=2 in formula (1)) was 75 parts by mol, the amount of tetrasulfide (X=3 in formula (1)) was 15 parts by mol. The amount of each repeating unit was confirmed by $^1$H-NMR.

The sulfide compound thus obtained had a weight average molecular weight of 20000 and a number average molecular weight of 5000. Weight average molecular weight and number average molecular weight were measured by GPC (LC-10A system, manufactured by Shimadzu Corporation) with Shodex KF804, KF803, KF802, and KF801 (manufactured by Showa Denko KK) as columns and tetrahydrofuran as an eluent. The measurement was carried out at a temperature of 40° C. in a column oven and the molecular weights were calculated based on standard polystyrene.

Synthesis Example 2

A sulfide compound was obtained in the same manner as in Synthesis Example 1 except that the amount of chlorine gas was changed to 37 g.

As to the amount of each repeating unit in the sulfide compound obtained by the above, per 100 parts by mol of the total amount of repeating unit (1) in the sulfide compound having a repeating unit (1), the amount of disulfide (X=1 in formula (1)) was 6 parts by mol, the amount of trisulfide (X=2 in formula (1)) was 64 parts by mol, the amount of tetrasulfide (X=3 in formula (1)) was 30 parts by mol. The amount of each repeating unit was confirmed by $^1$H-NMR.

Synthesis Example 3

A sulfide compound was obtained in the same manner as in Synthesis Example 1 except that the amount of chlorine gas was changed to 31 g.

As to the amount of each repeating unit in the sulfide compound obtained by the above, per 100 parts by mol of the total amount of repeating unit (1) in the sulfide compound having a repeating unit (1), the amount of disulfide (X=1 in formula (1)) was 5 parts by mol, the amount of trisulfide (X=2 in formula (1)) was 55 parts by mol, the amount of tetrasulfide (X=3 in formula (1)) was 40 parts by mol. The amount of each repeating unit was confirmed by $^1$H-NMR.

Synthesis Example 4

150 g (1.1 mol) of bis(2-mercaptoethyl)ether and 370 g of monochlorobenzene were added to a 1000 mL four-necked flask, and the liquid temperature was cooled to 20° C. Subsequently, 147 g of sulfur monochloride was added dropwise to the mixture of bis(2-mercaptoethyl)ether and monochlorobenzene over 4 hours while keeping the liquid temperature at 20° C. The solvent of the obtained reaction solution was removed by distillation under reduced pressure to obtain a sulfide compound. The amount of each repeating unit was confirmed by $^1$H-NMR. As to the amount of each repeating unit in the sulfide compound obtained by the above, per 100 parts by mol of the total amount of repeating unit (1), the amount of disulfide (X=1 in formula (1)) was 2 parts by mol, the amount of trisulfide (X=2 in formula (1)) was 23 parts by mol, the amount of tetrasulfide (X=3 in formula (1)) was 75 parts by mol. The amount of each repeating unit was confirmed by $^1$H-NMR.

Synthesis Example 5

A sulfide compound was obtained in the same manner as in Synthesis Example 1 except that the amount of chlorine gas was changed to 25 g.

As to the amount of each repeating unit in the sulfide compound obtained by the above, per 100 parts by mol of the total amount of repeating unit (1) having X=1, 2 or 3, the amount of disulfide (X=1 in formula (1)) was 4 parts by mol, the amount of trisulfide (X=2 in formula (1)) was 45 parts by mol, the amount of tetrasulfide (X=3 in formula (1)) was 51 parts by mol. Further, the repeating unit having Y=0 or at least 4 represented by formula (2) in the sulfide compound was 5 parts by mol per 100 parts by mol of the total amount of repeating unit (1). The amount of each repeating unit was confirmed by $^1$H-NMR.

Synthesis Example 6

A sulfide compound was obtained in the same manner as in Synthesis Example 1 except that the amount of toluene was changed to 200 g.

As to the amount of each repeating unit in the sulfide compound obtained by the above, per 100 parts by mol of the total amount of repeating unit (1) having X=1, 2 or 3, the amount of disulfide (X=1 in formula (1)) was 5 parts by mol, the amount of trisulfide (X=2 in formula (1)) was 75 parts by mol, the amount of tetrasulfide (X=3 in formula (1)) was 20 parts by mol. Further, the repeating unit having Y=0 or at least 4 represented by formula (2) in the sulfide compound was 10 parts by mol per 100 parts by mol of the total amount of repeating unit (1). The amount of each repeating unit was confirmed by $^1$H-NMR.

Examples 1 to 11, Comparative Examples 1 to 6

Preparation of Sample

The sulfide compounds obtained in Synthesis Examples 1 to 6 were used as additives for rubber. The mixing ratio of the rubber composition in each sample is as shown in Tables 1 and 2. Incidentally, NR shown in Tables 1 and 3 denotes natural rubber, and SBR shown in Table 2 denotes synthetic rubber. NR1 in Table 1 is a formulation according to JIS K 6352-2005, and SBR in Table 2 is a formulation according to JIS K 6383-2001.

In the Tables, "TBBS" is N-(tert-butyl)-2-benzothiazole sulfenamide, "MBTS" is di-2-benzothiazolyl disulfide, "DBATD" is 2-(dibutylamino)-1,3,5-triazine-4,6-dithiol.

In evaluating the mechanical properties, a rubber test sample was prepared from the obtained rubber composition in accordance with JIS K 6299-2012.

As a comparative example, a sample where sulfur was added as an additive for rubber in place of the sulfide compound (vulcanizing agent) obtained in Synthesis Example was also prepared.

TABLE 1

| NR1 | |
|---|---|
| | (g) |
| NR | 100 |
| Zinc oxide (Zinc white type II) | 5 |
| Stearic acid | 2 |
| Carbon black (HAF(N330)Asahi#70) | 35 |
| Vulcanization accelerator (TBBS) | 0.7 |
| Vulcanizing agent (Sulfide compound obtained in Synthesis Example) | 2.25 |

JIS K 6352-2005

TABLE 2

| SBR | |
|---|---|
| | (g) |
| SBR | 100 |
| Zinc oxide (Zinc white type II) | 3 |
| Stearic acid | 1 |
| Carbon Black (HAF(N330)Asahi#70) | 50 |
| Vulcanization accelerator (TBBS) | 1 |
| Vulcanizing agent (Sulfide compound obtained in Synthesis Example) | 1.75 |

JIS K 6383-2001

TABLE 3

| NR2 | |
|---|---|
| | (g) |
| NR | 100 |
| Zinc white type II | 5 |
| Stearic acid | 1 |

TABLE 3-continued

| NR2 | |
|---|---|
| | (g) |
| HAF(N330)Asahi#70 | 50 |
| DBATD | 0.5 |
| MBTS | 0.5 |
| Vulcanizing agent | 3 |
| (Sulfide compound obtained in Synthesis Example) | |

JIS K 6352-2005

[Evaluation of Reversion]

The test method for vulcanization characteristics with vulcanization tester was in accordance with JIS K 6300-2-2001. More specifically, according to JIS K6300-2-2001, the vulcanization curve of the obtained rubber composition where the horizontal axis is the vulcanization time and the vertical axis is the obtained torque was measured with a rotorless vulcanization tester as a rheometer at a predetermined test temperature. For the composition comprising natural rubber (NR), the test temperature was 160° C.

FIG. 1 shows a vulcanization curve of a rubber composition comprising natural rubber (NR) having a blending ratio shown in Table 1 (NR 1). For example, since the elastic torque gradually decreased after reaching the peak in Comparative Example 2 of FIG. 1, it is considered that vulcanization reversion was occurred. On the other hand, no decrease in elastic torque was observed in each Example, indicating that the anti-reversion property was improved by the additive for rubber of the present invention.

[Evaluation of Mechanical Properties]

A test for 100% tensile stress and a test for elongation at break of vulcanized rubber were conducted in accordance with JIS K 6251-1993.

The measurement results for each sample are shown in Tables 4, 5 and 6.

The aging test method of each sample was in accordance with JIS K 6257-1993. For example, heat aging of a sample comprising natural rubber (NR) was performed in an environment of 70° C. over 72 hours. On the other hand, heat aging of a sample comprising synthetic rubber (SBR) was carried out in an environment of 100° C. over 72 hours.

Taking 100% tensile stress as an example, "change rate (%)" described in the Table can be calculated from

[(100% tensile stress after aging−100% tensile stress before aging)/100% tensile stress before aging]×100.

"Change rate (%)" in test for elongation at break can be also calculated in the same way as above.

TABLE 4

| | NR1 | | | | | | | |
|---|---|---|---|---|---|---|---|---|
| | Amount of each repeating unit (parts by mol) | | | 100% tensile stress | | | Elongation at break | | |
| | | | | Before aging | After aging | Change rate | Before aging | After aging | Change rate |
| | X = 1 | X = 2 | X = 3 | (MPa) | (MPa) | (%) | (%) | (%) | (%) |
| Ex. 1 | 10 | 75 | 15 | 1.04 | 1.08 | 4 | 520 | 510 | −2 |
| Ex. 2 | 6 | 64 | 30 | 1.18 | 1.17 | −1 | 510 | 480 | −6 |
| Ex. 3 | 5 | 55 | 40 | 1.17 | 1.14 | −3 | 520 | 510 | −2 |
| Com. Ex. 1 | 2 | 23 | 75 | 1.26 | 0.8 | −37 | 530 | 400 | −25 |
| Com. Ex. 2 | Sulfur only | | | 2.56 | 3.11 | 21 | 520 | 490 | −6 |

*Heat aging condition: 70° C./72 hours

TABLE 5

| | SBR | | | | | | | |
|---|---|---|---|---|---|---|---|---|
| | Amount of each repeating unit (parts by mol) | | | 100% tensile stress | | | Elongation at break | | |
| | | | | Before aging | After aging | Change rate | Before aging | After aging | Change rate |
| | X = 1 | X = 2 | X = 3 | (MPa) | (MPa) | (%) | (%) | (%) | (%) |
| Ex. 4 | 10 | 75 | 15 | 1.69 | 1.92 | 14 | 730 | 710 | −3 |
| Ex. 5 | 6 | 64 | 30 | 1.76 | 2.11 | 20 | 740 | 680 | −8 |
| Ex. 6 | 5 | 55 | 40 | 1.77 | 2.12 | 20 | 730 | 680 | −7 |
| Com. Ex. 3 | 2 | 23 | 75 | 2.00 | 2.8 | 40 | 670 | 500 | −25 |
| Com. Ex. 4 | Sulfur only | | | 3.97 | 8.98 | 126 | 450 | 190 | −58 |

*Heat Aging Condition: 100° C./72 hours

TABLE 6

| | Amount of Each Repeating Unit (parts by mol) | | | 100% tensile stress | | | Elongation at break | | |
|---|---|---|---|---|---|---|---|---|---|
| | | | | Before aging | After aging | Change rate | Before aging | After aging | Change rate |
| | X = 1 | X = 2 | X = 3 | (MPa) | (MPa) | (%) | (%) | (%) | (%) |
| Ex. 7 | 10 | 75 | 15 | 4.35 | 7.93 | 82 | 509 | 385 | −24 |
| Ex. 8 | 6 | 64 | 30 | 4.42 | 8.03 | 82 | 503 | 384 | −24 |
| Ex. 9 | 5 | 55 | 40 | 4.83 | 8.82 | 83 | 501 | 373 | −26 |
| Ex. 10 | 4 | 45 | 51 | 5.26 | 9.32 | 77 | 494 | 373 | −24 |
| Ex. 11 | 5 | 75 | 20 | 4.38 | 8.01 | 83 | 505 | 383 | −24 |
| Com. Ex. 5 | 2 | 23 | 75 | 6.09 | 12.32 | 102 | 494 | 337 | −32 |
| Com. Ex. 6 | Sulfur only | | | 5.77 | 12.38 | 115 | 483 | 290 | −40 |

*Heat Aging Condition: 100° C./72 hours

The additive for rubber of the present invention can impart good heat resistance and can further impart good aging resistance. Furthermore, the additive for rubber of the present invention does not cause or hardly cause reversion. In addition, the additive for rubber of the present invention has good mechanical properties and can also reduce environmental burden.

In addition, the rubber products comprising the additive for rubbers of the present invention can also have good aging resistance, heat resistance and mechanical properties.

INDUSTRIAL APPLICABILITY

The additive for rubber of the present invention can impart good heat resistance and mechanical properties to rubber products such as tires.

The invention claimed is:

1. An additive for rubber comprising a sulfide composition,
wherein the sulfide composition comprises a sulfide compound having a repeating unit represented by formula (1),
wherein, in the sulfide compound, the amount of repeating unit (1) having X=1 is 1 parts by mol to 40 parts by mol, the amount of repeating unit (1) having X=2 is at least 45 parts by mol and the amount of repeating unit (1) having X=3 is 4 parts by mol to 54 parts by mol per 100 parts by mol of the total amount of repeating unit (1),
wherein n meaning the number of repeating unit (1) in the sulfide compound is 1 to 400;

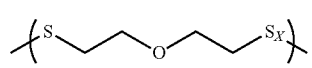

(1)

wherein X is 1, 2 or 3.

2. The additive for rubber according to claim 1,
wherein, in the sulfide compound, the amount of repeating unit (1) having X=2 is at least 50 parts by mol per 100 parts by mol of the total amount of repeating unit (1).

3. The additive for rubber according to claim 2,
wherein, in the sulfide compound, the amount of repeating unit (1) having X=1 is 1 parts by mol to 20 parts by mol per 100 parts by mol of the total amount of repeating unit (1).

4. The additive for rubber according to claim 2,
wherein the sulfide compound further has a repeating unit represented by formula (2),
wherein the amount of repeating unit (2) is at most 15 parts by mol per 100 parts by mol of the total amount of repeating unit (1) comprised in the sulfide compound:

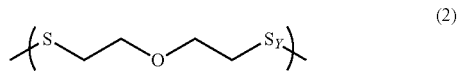

(2)

wherein Y is 0 or an integer of at least 4.

5. The additive for rubber according to claim 1,
wherein, in the sulfide compound, the amount of repeating unit (1) having X=1 is 1 parts by mol to 20 parts by mol per 100 parts by mol of the total amount of repeating unit (1).

6. The additive for rubber according to claim 5,
wherein the sulfide compound further has a repeating unit represented by formula (2),
wherein the amount of repeating unit (2) is at Most 15 parts by mol per 100 parts by triol of the total amount of repeating unit (1) comprised in the sulfide compound:

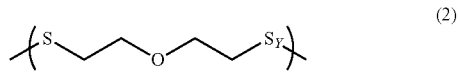

(2)

wherein Y is 0 or an integer of at least 4.

7. The additive for rubber according to claim 1,
wherein the sulfide compound further has a repeating unit represented by formula (2),
wherein the amount of repeating unit (2) is at most 15 parts by mol per 100 parts by mol of the total amount of repeating unit (1) comprised in the sulfide compound:

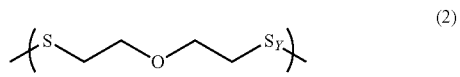

(2)

wherein Y is 0 or an integer of at least 4.

8. The additive for rubber according to claim 7, wherein the sulfide compound consists of repeating unit (1) and repeating unit (2).

9. The additive for rubber according to claim 7, wherein at least 75% mass of the sulfide compound is repeating unit (1) and repeating unit (2).

10. The additive for rubber according to claim 1, wherein, in the sulfide compound, the amount of repeating unit (1) having X=3 is 4 parts by mol to 40 parts by mol per 100 parts by mol of the total amount of repeating unit (1).

11. The additive for rubber according to claim 1, wherein n is 6-400.

12. The additive for rubber according to claim 1, wherein n is 10 to 200.

13. The additive for rubber according to claim 1, wherein, in the sulfide compound, the amount of repeating unit (1) having X=1 is 1 parts by mol to 20 parts by mol per 100 parts by mol of the total amount of repeating unit (1) and the amount of repeating unit (1) having X=2 is 55 parts by mol to 95 parts by mol per 100 parts by mol of the total amount of repeating unit (1).

14. The additive for rubber according to claim 1, wherein, in the sulfide compound, the amount of repeating unit (1) having X=3 is larger than the amount of repeating unit (1) having X=1.

15. The additive for rubber according to claim 1, wherein, in the sulfide compound, the ratio of the amount of repeating unit (1) having X=3 to the amount of repeating unit (1) having X=1 is 1.1:1 to 10:1.

16. A method for producing the additive for rubber according to claim 1 comprising a step of reacting bis(2-mercaptoethyl)ether with sulfur dichloride to produce the sulfide compound having a repeating unit represented by formula (1).

17. A rubber composition comprising the additive for rubber according to claim 1 and natural rubber and/or synthetic rubber.

18. A rubber composition comprising the additive for rubber according to claim 2 and natural rubber and/or synthetic rubber.

19. A rubber composition comprising the additive for rubber according to claim 5 and natural rubber and/or synthetic rubber.

20. A rubber composition comprising the additive for rubber according to claim 7 and natural rubber and/or synthetic rubber.

\* \* \* \* \*